United States Patent [19]
Hadley

[11] Patent Number: 6,051,555
[45] Date of Patent: Apr. 18, 2000

[54] STIMULATING SEXUAL RESPONSE IN FEMALES

[76] Inventor: Mac E. Hadley, 1921 Calle Campana de Plata, Tucson, Ariz. 85745

[21] Appl. No.: 09/179,225

[22] Filed: Oct. 27, 1998

Related U.S. Application Data

[63] Continuation of application No. 08/699,571, Aug. 19, 1996, abandoned, which is a continuation of application No. 08/264,921, Jun. 24, 1994, Pat. No. 5,576,290, which is a continuation of application No. 08/043,159, Apr. 5, 1993, abandoned.

[51] Int. Cl.$^7$ ........................... A61K 38/08; A61K 38/12
[52] U.S. Cl. ................................. 514/11; 514/16
[58] Field of Search .................... 814/9, 11, 15, 814/16; 930/DIG. 572, DIG. 582; 530/312, 317, 321, 328, 329

[56] References Cited

U.S. PATENT DOCUMENTS 5,576,290  11/1996  Hadley ....................................... 514/11
5,674,839  10/1997  Hruby et al. ................................. 514/9
5,714,576  2/1998   Hruby et al. ............................. 530/312

FOREIGN PATENT DOCUMENTS 292291  11/1988  European Pat. Off. .

OTHER PUBLICATIONS

Al–Obeidi et al. Potent and Prolonged Acting Cyclic Lactam Analogues . . . J. Med. Chem. vol. 32, No. 12, pp. 2555–2561, 1989.

Hadley et al. Linear and Cyclic α–Melanotropin . . . Pigment Cell Research, vol. 2, No. 6, pp. 478–484, 1989.

*Primary Examiner*—Jeffrey E. Russel
*Attorney, Agent, or Firm*—Yahwak & Associates

[57] ABSTRACT

The present invention is directed to a series of peptides which may be used for stimulating sexual response in females.

8 Claims, No Drawings

STIMULATING SEXUAL RESPONSE IN FEMALES

This is a continuation of my earlier U.S. patent application Ser. No. 08/699,571, filed Aug. 19, 1996, now abandoned which in turn is a continuation of U.S. patent application Ser. No. 08/264,921, filed Jun. 24, 1994, now U.S. Pat. No. 5,576,290, which is turn is a continuation application of U.S. patent application Ser. No. 08/043,159, filed Apr. 5, 1993, and now abandoned.

Erectile dysfunction, or impotence, is probably the most common male sexual symptom encountered by the practicing physician, and an improved understanding of the problem and new approaches to diagnosis and treatment have greatly increased the chances of helping patients with this problem.

Erection of the penis is in most simple terms a hydraulic event in which vascular channels that are empty in the flaccid penis become filled with blood at pressures approaching systemic levels. Erection occurs when the arteriolar and sinusoidal smooth muscles of the vessels within the corpora relax, thus lowering resistance in these channels and allowing arterial blood to surge into the penis. However, exit of the arterial blood is impeded by an increase in venous resistance. Further distention of the sinusoids is restrained by the minimally distensible tunica albuginea that raises the pressure further and also restricts venous outflow. Thus, the corpora cavernosa and corpus spongiosum can be filled with blood and the penis can be erect without placing much demand on cardiac output. Although many details remain unclear, increasing evidence indicates that vasoactive intestinal polypeptide, perhaps aided by alpha-adrenergic blockade, acetylcholine, and nitric oxide controls the vascular changes that occur during erection.

At least three controls of erection are of clinical importance: the availability of adequate arterial inflow from the aortoiliac system; a neurologic control that involves two pathways—the reflexogenic in which the pudendal nerve serves as an afferent and the parasympathetic fibers act as efferents, and the erotogenic which are highly complex and include multiple afferent pathways, unknown central connections, and sympathetic outflow via the 10th dorsal nerves through the second lumbar segments; and the third control of normal erection is a central nervous system control based upon hormonal testosterone that is required for the development of libido and neural control of the penis.

Erectile dysfunction is defined medically as the inability to develop and sustain an erection adequate for intercourse for at least 25 percent of attempts. The differential diagnosis of erectile dysfunction is best approached by considering the normal controls of erection, for example, major vascular insufficiency as a cause of inadequate erection occurs with aortoiliac atherosclerosis; it is usually accompanied by claudication and by diminished or absent femoral pulses.

The possibility that disease of smaller arteries is causing erectile dysfunction can be pursued with modern hemodynamic techniques. If injection of papaverine into the corpora cavernosa induces a normal erection within 10 minutes, there is no need for further evaluation of the vascular component; doppler and ultrasound study can delineate arterial, sinusoidal, or venous inadequacy. However, as these methods are not widely available, the differential diagnosis is still guided by clinical findings.

Peripheral neurogenic erectile dysfunction occurs as a result of spinal cord trauma, in the various syndromes of autonomic insufficiency, and in about 50 percent of males with insulin-dependent diabetes mellitus. In diabetes, the history usually discloses other signs of neuropathy such as postural hypotension, diarrhea, and incontinence. The erectile defect associated with diabetes may be an impairment of the relaxation of smooth muscle of the corpora cavernosa. In vitro, this response was shown to be impaired by either direct electric or neurochemical stimulation. The absence of nocturnal penile tumescence has been used for identifying cases of neurologic impotence.

Antihypertensive drugs, tranquilizers, antidepressants, and many other agents may all cause decreased erectile capacity. Hypertension and antihypertensive medications are frequent causes of impotence. In one group of hypertensive patients, 17 percent reported some decrease in potency before any treatment. Diuretics, centrally active sympatholytics, Beta blockers, and peripherally active agents may all induce partial or complete impotence. The mechanisms by which these drugs produce impotence are not well understood, and it is impossible to predict which agent will affect which patient. It has been, therefore, prior to the making of the present invention, necessary to use trial and error to distinguish between the pharmacological causes of impotence and the psychological influences of the disease and its treatment.

Alcohol can cause erectile dysfunction by many mechanisms, but it is extremely difficult to untangle its pharmacological effects from its emotional and social impact. Erectile dysfunction may also accompany temporal lobe epilepsy—some patients may have hyperprolactinemia, but in others the difficulty has no obvious cause and may reflect abnormalities in still unknown pathways associated with proper function.

Psychogenic factors are thought to be the most frequent causes of impotence. Anxiety, fatigue, interpersonal stresses, and chronic illness are common underlying factors. Depression requires separate mention because of its frequency; impotence may be the presenting complaint that leads to correct diagnosis and treatment. Patients with psychogenic impotence are often capable of erection in some circumstances—for example, when masturbating or when having sex with a different partner. Endocrine impotence (which include abnormalities including testosterone deficiency from pituitary or testicular disease, estrogen excess and hyperprolactinemic syndromes, for example), on the other hand, tends to develop gradually and then to be constant.

As specific treatable causes of erectile dysfunction are defined, it becomes imperative to follow a protocol capable of detecting the principal cause of dysfunction in each patient. The starting point is a careful history and physical examination, combined with a detailed sexual history. The patient should be asked about duration of the symptom, the circumstances in which it is manifested, the potential role of disease or medication, and the possibility of alcoholism or depression. Physical examination should include testing peripheral reflexes and pinprick sensation in the perianal area. If any of the specific conditions already mentioned is suggested, the appropriate therapy is clear. In many patients suffering from this condition no clear etiology is determined, and in those two additional tests are conventionally indicated.

The "gold standard" for noninvasive testing is the recording of nocturnal penile tumescence. This test can be done in a sleep laboratory and several devices are available for home use. By such tests, one can distinguish between the presence of some erection and the sustained achievement of sufficient pressure for vaginal penetration. Alternatively, prior to the present invention, the physician can inject, directly into the penile corpora, either papaverine, papaverine plus phentolamine, or prostaglandin El. A firm erection achieved in this way indicates that the vascular component of erection is adequate and also provides a somewhat effective therapeutic alternative. Any failure to induce erection should be followed by definitive vascular studies.

The appropriate therapy for erectile dysfunction of a nonspecific cause allows for several options. Injection of papaverine alone or combined with phentolamine, as indicated above, will induce an erection lasting 30 to 120 minutes in about 70% of patients. However, side effects include pain, ecchymosis, and occasional episodes of priapism (a condition which is characterized by a persistent erection that cannot be relieved by sexual intercourse or masturbation) that require pharmacological intervention. This approach to relief of erectile dysfunction is still experimental, but is widely used. The present invention provides the possible advantage of "synergistic polypharmacology" whereby lower intracorporeal (penile) injections may be used, and thus eliminate the problem of unwanted priapism often associated with papavaine and other locally injected drugs.

While there is presently no consensus treatment for sexual dysfunction in the male, most drug strategies are directed as though the defect were primary (at the level of the penis) in origin, however, that is seldom the cause. Most drug therapies involve autoinjection (intracorporeal) of a drug which is directed at inhibiting sympathetic (α-adrenoceptor) activity and causing muscle (sphincter) relaxation. As noted above, papaverine is most often utilized in drug therapies for this dysfunction and functions as a nonspecific relaxant of smooth muscle. The prostaglandins, specifically those belonging to the E-series, are also sometimes employed in drug therapies because of their smooth muscle relaxant effect on erectile tissue. Although vasoactive intestinal peptide has been used in trials to induce erection, intrapenile injections of the peptide have proven ineffective in inducing a full erection necessary for intercourse. Nitric oxide (a gas) is now considered to be a physiological mediator of erection, but it is difficult to envision how it might be applied effectively to the penis to achieve a satisfactory erection.

An alternative to this invasive approach is the use of a plastic tube and suction pump to create a vacuum around the penis. When erection results, a rubber band is placed at the base of the penis, and satisfactory coitus is thus possible. An additional choice is surgical implantation of one of several types of prostheses, and these have been used successfully by many couples. Finally, sex therapy is of considerable use for psychogenic impotence; in addition, supportive counseling and reassurance are necessary adjunct for all patients with erectile dysfunction, particularly because anxiety and fear of failure compound any partial erectile difficulty.

Although these approaches to overcome erectile dysfunction are better than none, it would preferable if the therapy did not involve any invasive procedures such as direct injection into the penis or implantation of a prostheses, and relied instead upon less traumatic methodologies. In the early 1980s, a few hundred men who took the oral drug trazodone for depression unexpectedly experienced prolonged and painful erections. In a few cases surgery was required in order to halt the erection. This makes trazodone the first oral drug that has been discovered to prolong erections. Although its side effects are such that trazodone is not an acceptable therapy for sexual dysfunction, it does indicate that alternative less invasive routes of administration are possible for the treatment of such conditions.

While the present psychopharmacologic approach for treatment encompasses drug therapies that primarily affect the behavioral components of the sexual response, i.e., sex drive or libido, through the alteration of neuronal activity within the brain, this effect is not restricted to sexual drive because augmentation of neuronal activity within the brain areas regulating sexual drive has been shown to lower response thresholds for the erectile reflex. In fact, an interaction between spinal and supraspinal centers is mandatory for normal erectile function. The neuropharmacologic approach also encompasses drug-induced changes in neuronal activity, but the site of action may include the brain, brainstem, spinal chord and/or peripheral nerve fibers, and the primary effects are restricted to the alteration of spinal reflex function. The vascular pharmacologic approach encompasses any pharmacologic approach that alters smooth muscle responses of the penile vasculature.

Some drugs work centrally, that is their actions are at the level of the central nervous system. Activation of central nervous system opiate pathways appears to be inhibitory to erectile function, whereas inhibition of opiate receptors appear to be stimulatory to such activity. Oxytocin appears to be a central stimulant of erectile function, and there is evidence that apomorphine (a dopamine agonist) induces penile erection by releasing oxytocin in the central nervous system. The clinical applicability of apomorphine is, however, partially limited by side effects and a short duration of action. Most interesting, both oxytocin and ACTH/MSH-like molecules induce an erection when injected into the third ventricles of the brain in rodent studies. It is of interest that in the rodent, MSH-like peptides cause stretching and yawning behavior, a similar phenomenon which was seen in the volunteers who received compounds according to the present invention. Thus, it can be surmised that the actions of the compounds according to the present invention are probably not at the level of the penis, but rather act upon neurons of the CNS.

In view of the problems associated with distinguishing psychogenic impotence from organic or vascular insufficiency, alternative approaches to those presently in use are still required by the physician.

It is one aspect of the present invention, therefore, to describe a means of distinguishing psychogenic impotence from sexual dysfunction brought about by organic pathologies or vascular insufficiencies.

It is a second aspect of the present invention to provide a male with a means to overcome sexual dysfunction caused for psychogenic reasons.

It is still another aspect of the present invention to describe a series of compounds active in bringing about an enhancement of libido (either by overcoming psychogenic sexual dysfunction in males or by inducing sexual receptivity in females) in animals (specifically in mammals, and more specifically in, but not limited to, humans) which may be administered by surgically invasive, for example injection, or by non-invasive methods, for example by ocular, oral or other routes of administration.

These and other aspects of the present invention will become more readily apparent in the following detailed description and examples.

The structure of the linear and cyclic peptides which comprise the biologically active compounds of the present invention are:

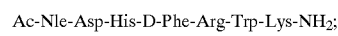

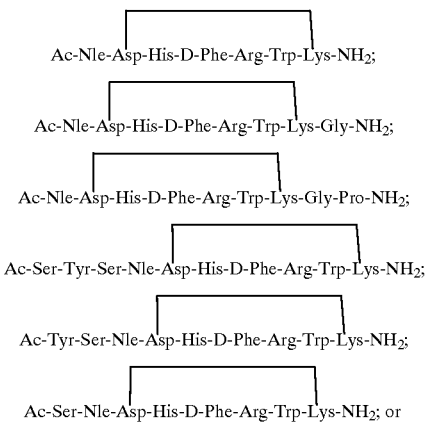

Ac-Nle-Asp-His-D-Phe-Arg-Trp-Lys-NH$_2$;

Ac-Nle-Asp-His-D-Phe-Arg-Trp-Lys-Gly-NH$_2$;

Ac-Nle-Asp-His-D-Phe-Arg-Trp-Lys-Gly-Pro-NH$_2$;

Ac-Ser-Tyr-Ser-Nle-Asp-His-D-Phe-Arg-Trp-Lys-NH$_2$;

Ac-Tyr-Ser-Nle-Asp-His-D-Phe-Arg-Trp-Lys-NH$_2$;

Ac-Ser-Nle-Asp-His-D-Phe-Arg-Trp-Lys-NH$_2$; or mixtures thereof.

In this listing of compounds according to the present invention, the amino acid residues have their conventional meaning. Thus, "Nle" refers to norleucine; "Asp" refers to aspartic acid; "His" refers to histidine; "D-Phe" refers to D-phenylalanine; "Arg" refers to arginine; "Trp" refers to tryptophan; "Lys" refers to lysine; "Gly" refers to glycine; "Pro" refers to proline; "Tyr" refers to tyrosine, and "Ser" refers to serine.

The linear compounds of the present invention may be synthesized by solid-phase synthesis and purified according, for example, to the basic methods described by Sawyer et al [see P.N.A.S. USA 77:5754 (1980); P.N.A.S. USA 79:1751 (1982); or J. Med. Chem. 25:1022 (1982)], and the specific methods described by Al-Obeidi et al [see J. Med. Chem. 32:174 (1989), and J. Med. Chem. 32:25555 (1989)].

Briefly summarized, each compound was synthesized by first preparing a p-methylbenzhydrylamine resin to which the desired amino acids were coupled, successively, as its N$^\alpha$-Boc derivative ("Boc" refers to t-butyloxycarbonyl). The reactive side chain side group of each tri-functional amino acid was protected by incorporation of an appropriate protective group as is well known in the peptide art. After all the amino acid residues were coupled to the resin, the amino terminus of the peptide-resin was acetylated, the protective peptide was cleaved from the resin, and all protecting groups were removed. The crude compound was then purified by ion-exchange chromatography on silica gel using appropriate solvents. Optical rotation values were used as a check and were measured at the mercury/green line (546 nm) in a Perkin-Elmer 241 MC Polarimeter.

In addition to this briefly summarized procedure, other well known procedures utilizing other resins and reagents may be used to prepare the compounds according to the present invention. For ease and reliability of manufacture, however, it is preferred that automated solid-phase chemistries be used in the synthesis of compounds according to the present invention.

More particularly, the linear compounds according to the present invention were generally prepared according to the following example.

EXAMPLE I

Ac-Nle-Asp-His-D-Phe-Arg-Lys-NH$_2$

This compound was prepared by coupling N$^\alpha$-Boc-Lys-(N$^\epsilon$2Clz) to p-methylbenzhydrylamine resin (2.0 gr pMBHA resin, o.7 mmol NH$_2$/gr of resin) using 3-fold excess of amino acid using solid-phase methods of peptide synthesis. After 90 minutes, the resin was washed with dichloromethane, neutralized, and the amino acid group acetylated with acetic anhydride-pyridine mixture. No reactive amino groups on the resin were detected by the ninhydrin test after 30 minutes. A cycle for coupling of each amino acid residue onto the growing peptide chain consisted of the following: (1) Washing with four 30-ml portions of CH$_2$Cl$_2$, 2 min /wash; (2) Cleavage of the Boc group by 30 ml of 48% trifluoroacetic acid in dichloromethane containing 2% anisole, one treatment for 5 min, a second for 20 min; (3) Washing with four 30-ml portions of dichloromethane, 2 min/wash; (4) Neutralization by the addition of two 30-ml portions of 10% diisopropylethylamine in dichloromethane, and shaking for 2 min wash; (5) Washing with four 30-ml portions of dichloromethane, 2 min/wash; (6) Addition of 3-fold excess of the Boc amino acid derivative in 5 ml of dichloromethane, 2.4 ml of N-hydroxybenzotriazole (HOBt) of 1 mmol/ml solution of HOBt in DMF (except in the case of N-Boc-N$^{im}$ Tos-His; the term "N$^{im}$Tos" refers to N-imidazole tosyl), followed by 2.4 ml of dicyclohexylcarbodiimide (DCC) of 1 mmol/ml solution of DCC in DMF. The mixture was then shook for 2–3 hrs. (in the case of Trp, Arg and His, DMF was used as a coupling solvent); (7) After completion of the coupling (ninhydrin negative) washing with three 30-ml portions of dichloromethane, 2 min/wash; (8) Washing with 3 ml portion of 100% ethanol, 2 min/wash; (9) Washing with four 30-ml portions of dichloromethane, 1 min/wash. The protected peptide resin corresponding to the title compound was obtained after stepwise coupling of the following N$^\alpha$-Boc amino acids (or derivatives) (in order of addition): N$^\alpha$-Boc-N$^i$-For-Trp; N$^\alpha$-Boc-N$^\gamma$Tos-Arg; N$^\alpha$-Boc-D-Phe; N$^\alpha$-Boc-N$^{im}$Tos-His; N$^\alpha$-Boc-Asp (β Bzl); and N$^\alpha$-Boc-Nle. The derivatives in the coupling reaction are defined as follows: "N$^i$" refers to N-indolyl; "2 Cl$_2$" refers to 2-chlorobenzoyloxycarbonyl; "For" refers to formyl; and "N$^\gamma$" refers to N-guanidino. After coupling the last amino acid, the N$^\alpha$-Boc protection group was removed, the amino group neutralized, and acetylated with 2-fold excess of 1:1 mixture of acetic anhydride/pyridine in dichloromethane for 1 h. The Ac-Nle-Asp (β-Bzl)-His (N$^{im}$-Tos)-D-Phe-Arg (N$^\gamma$-Tos)-Trp-(N$^i$-For)-Lys(N$^\epsilon$-2-Clz)-p-MBHA resin was washed with dichloromethane and dried in vacuo to give 2.1 g. A 1.5 g sample of the protected peptide resin was cleaved by liquid HF and after evaporation of the volatile materials, the dried, cleaned peptide was washed with 3×30 ml of anhydrous diethyl ether and extracted with 3×30 ml of 30% aqueous HoAc. The residue was lyophilized to yield crude peptide which was then dissolved in 2 ml of NH$_2$OAc buffer (pH 4.5), and filtered through a cartridge filter on the top of a carboxymethyl cellulose column. The major peak was collected and lyophilized to give a white powder. 112 mg of the CMC chromatographically pure powder was purified by HPLC to give 64 mg of pure title peptide.

The solid-phase peptide synthesis of cyclic peptide analogues, according to the present invention, were conducted by conventional solid-phase synthesis techniques. Briefly summarized, N$^\alpha$-tert-butyloxycarbonyl protected amino acids and their derivatives were coupled to a p-methylbenzhydrylamine resin with 3-fold excess of the Boc-protected amino acid derivative, a 2.4-fold excess of N-hydroxybenzotriazole (HOBt) of 1 mmol/ml solution in DMF (except in case of His), and a 2.4-fold excess of 1 mmol/ml solution of dicyclohexylcarbodiimide in DMF. The coupling reaction was carried out in dichloromethane for a 1 to 3 hour period and monitored by ninhydrin and/or chloranil tests which were repeated as necessary. Reactive side chains of amino acids were protected as follows: Lys 2,4-dichlorobenzyloxycarbonyl: Trp, formyl; Arg, tosyl; His, tosyl; Glu and Asp, Benzyl ester. Cleavage of the N-Boc protecting group was performed by treatment with 48% trifluoroacetic acid containing 2% anisole in dichloromethane for 5 and 20 min each.

A cycle for the incorporation of each amino acid residue into the growing peptide chain consists of the following: (1) washing with $CH_2Cl_2$ (4×30 ml, 1 min/wash), (2) Boc protection was removed at each step by two treatments with 48% TFA in $CH_2Cl_2$ containing 2% anisole for 5 and 20 min each; (3) washing with $CH_2Cl_2$ (2×30 ml); (4) neutralizing with 10% diisoprophylethylamine in $CH_2Cl_2$ (2×30 ml, 3 min/wash); (5) washing with $CH_2Cl_2$ (3×30 ml, 2 min/wash); (6) adding the Boc-protected amino acid derivative in 20 ml of $CH_2Cl_2$ (except in the cases of Trp, Arg and His when DMF was substituted for $CH_2Cl_2$ because of solubility), followed by HOBt, followed by DCC and shaking for 1–3 h; (7) washing with $CH_2Cl_2$ (3×30 ml, 2 min/wash); and (8) washing with 100% EtOH (3×30 ml, 2 min/wash). Completion of coupling was monitored, and after coupling the last amino acid, the $N^\alpha$-Boc protecting group was removed, the amino group neutralized, and acetylated with a 10-fold excess of N-acetylimidazole in $CH_2Cl_2$ or using 1:1 mixture of acetic anhydride:pyridine in $CH_2Cl_2$ (2-fold excess for 1 h).

Peptides were deprotected and removed from the resin with anhydrous liquid HF (10 ml/1 g of resin) containing 10% anisole and 8% 1,2-dithioethane at 0° C for 45 min. After evaporation of the volatile materials in vacuo, the free peptides were washed with diethylether or ethylacetate (3×30 ml) and then extracted with 30% aqueous solution of acetic acid (3×30 ml), and distilled water (3×30 ml). the combined aqueous extract was lyophilized to give a white powder of the crude peptide. Each peptide was purified by column chromatography on cation-exchange carboxymethyl cellulose resin, using discontinuous gradient of ammonium acetate buffer as follows: 250 ml of 0.01M $NH_4OAc$ (pH 4.5), 250 ml of 0.01M $NH_4OAc$ (pH 6.8), 250 ml of 0.1M $NH_4OAc$ (pH 6.8), and 250 ml of 0.2M $NH_4OAc$ (pH 6.8). The major peak (280 nm detection) eluted during the last part of 0.01M $NH_4OAc$ (pH 6.8) and the first half of the 0.1M $NH_4OAc$ (pH 6.8) buffer was lyophilized to give a purified peptide as a white powder.

More particularly, the cyclic compounds, according to the present invention, were prepared according to the following example:

EXAMPLE II

Ac-Nle-Asp-His-D-Phe-Arg-Trp-Lys-NH$_2$

From 1.4 g (0.5 mmol) of Boc-His ($N^{im}$-Tos)-D-Phe-Arg ($N^\gamma$-Tos)-Trp ($N^i$-For)-Lys ($N^\epsilon$-2,4-$Cl_2$Z)-p-MBHA resin prepared as in Example I, the protected peptide resin of the title compound was prepared by stepwise coupling of $N^\alpha$-Boc-Asp (β-Bzl) and $N^\alpha$-Boc-Nle. Each coupling reaction was achieved by following the same coupling scheme reported under the general solid-phase peptide methodology. After coupling the last amino acid, the $N^\alpha$-Boc protecting group was removed, the amino group neutralized, and acetylated with either a 10-fold excess of N-Acetylimidazole in dichloromethane (for 6–8 hrs.) or with a 2-fold excess of 1:1 mixture of acetic anhydride:pyridine in dichloromethane (for 1–2 hrs)to give the protected peptide resin Ac-Nle-Asp (β-Bzl)-His ($N^{im}$-Tos)-D-Phe-Arg ($N^\gamma$-Tos)-Trp ($N^i$-For)-Lys ($N^\epsilon$-2,4-$Cl_2$Z)-p-MBHA resin. A 1.0 g sample of the vacuum dried peptide resin was treated with 10 ml anhydrous HF in the presence of 1 ml anisole and 0.8 ml 1,2-dithioethane for 45 min at 0° C.

After the HF, anisole, and 1,2-dithioethane were evaporated in vacuo, the dried product mixture was washed with three 30 ml portions of diethylether, and the peptide was extracted with three 30 ml portions of 30% acetic acid. Upon lyophilization of the aqueous extract of the peptide 370 mg of the crude Ac-Nle-Asp-His-D-Phe-Arg-Trp-Lys-NH$_2$ was obtained. A portion of the crude heptapeptide (110 mg) was purified by a purification scheme which included dissolving the crude peptide in 2–4 ml of 0.01M $NH_4OAc$, pH 4.5, and chromatographed on carboxymethylcellulose column (2.0× 25.0 cm) with a discontinuous gradient (250 ml each) of 0.01 (pH 4.5), 0.01, and 0.02M $NH_4OAc$ (pH 6.8). The major peak detected at 280 mn was eluted during the first half of the 0.1M $NH_4OAc$ (pH 6.8) buffer and was lyophilized to give 82 mg of white powder of the linear peptide. A 40.0 mg of the pure linear product was subjected to cyclization by dissolving the pure linear peptide in 1 ml of 5% HCl aqueous solution and the solution chromatographed on diethylaminoethylcellulose (of hydrochloric acid form) column (1.0× 15.0 cm) with 100 ml of 5% HCl aqueous solution and the eluted peak monitored at 280 nm. Lyophilization of the collected peptide peak gave a linear peptide as the hydrochloride salt. The peptide salt was dissolved in 3 ml of dry DMF and secondary amine free DMF (distilled from ninhydrin under reduced pressure). To the peptide solution in DMF was added anhydrous $K_2HPO_4$, the reaction mixture was cooled in an ice-bath to 0° C., 17 ml of diphenylphosphorylazide was added, the reaction mixture stirred at 0° C., and then the whole reaction flask was transferred into the cold room at 12° C. The reaction mixture was stirred overnight at 12° C. and the completion of the reaction was monitored by HPLC (Vydac column, 25.0 cm×4.6 mm with 0.1% trifluoroacetic acid/$CH_3CN$). Also, the ninhydrin test was used to detect the completion of the cyclization. The cyclized product was purified, after quenching the reaction with 10% aqueous HOAc solution, by desalting on $P_4$ polyacrylamide column (80.0 cm×1.0 cm) using 30% HOAc and purified by semipreparative HPLC to give 12 mg of pure titled product. [see Al-Obeidi et al, supra].

In like manner, but with appropriate reagent substitution in accordance with known procedures the following peptides showing erectogenic activity were prepared and tested:

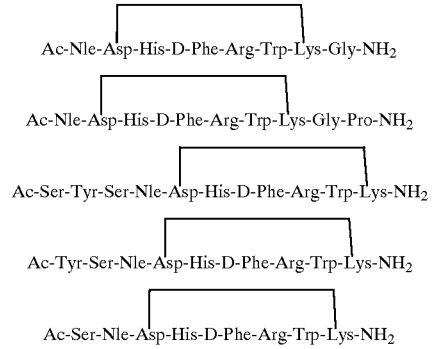

Ac-Nle-Asp-His-D-Phe-Arg-Trp-Lys-Gly-NH$_2$

Ac-Nle-Asp-His-D-Phe-Arg-Trp-Lys-Gly-Pro-NH$_2$

Ac-Ser-Tyr-Ser-Nle-Asp-His-D-Phe-Arg-Trp-Lys-NH$_2$

Ac-Tyr-Ser-Nle-Asp-His-D-Phe-Arg-Trp-Lys-NH$_2$

Ac-Ser-Nle-Asp-His-D-Phe-Arg-Trp-Lys-NH$_2$

Each of the peptides according to the present invention invariably induce an erection in the human male, and does so at a very low dose without any detectable side effects when administered systemically. The effect apparently takes place within the central nervous system. Therefore, erection induced by these peptides will allow the physician to determine whether CNS-derived impulses from the brain to the penis are intact. If so, then the sexual dysfunction can be ascribed as being psychogenic in nature. Failure to respond to the peptides according to the present invention might suggest a defect at the level of the penis or some higher spinal pathway. Used in combination with a local injection of a substance (e.g., papaverine) into the penis, then the true nature of the defect can be pinpointed.

Recent observations on the erectogenic properties of the biologically active peptides according to the present invention are given in the following example:

EXAMPLE III

The peptides described herein were prepared by sterile methods to a final concentration of 10 mg of peptide per ml of physiological saline. In addition to a full dose providing 10 mg of the peptide to the individual, doses of 0.1 to 0.3 ml (providing 1 mg to 3 mg of the peptide to each individual) of this stock material were also injected into volunteers, with a dose of 0.1 to 0.2 ml being the most often used dosage.

A 10 mg dose of the peptide identified in Example II was given subcutaneously in either the upper arm or inner thigh to a human volunteer resulted in an erection of 6 to 8 hours duration. The onset of erection occurred about 1 to 2 hours after injection. Half the dose (5 mg) of the peptide resulted in a continued tumescence of 4 to 6 hours duration as did a dose of 3.2 mg. A smaller dose of 2.5 mg resulted in an on-off erectile response of 2 to 6 hours duration. At the smallest dose administered (1.25 mg), generally no erectile activity was noted in the volunteers used for this testing. A dose of 3.75 mg given to volunteers produced a long lasting erection of 4 to 6 hour duration. At all concentrations that caused an exaggerated erectile response, stomach discomfort was noted. In some, this discomfort was considerable. At the lower doses of 1.25 to 2.5 mg which gave an erection, no stomach discomfort was noted. Accordingly, although dosages of from about 1.0 mg to about 10.0 mg show the desired activity according to the present invention, it is preferred that the lower ranges of dosage which bring about the desired erection without undesirable side effects be used. Accordingly, it is preferred that dosages of about 1.5 mg to 2.5 mg of peptide be provided when the route of administration is subcutaneous or intramuscular. With other routes of administration, this range may require adjustment, however, it is still preferred that the lower range of adjusted effective dosages for the selected route of administration be used.

Another of the peptides according to the present invention (Ac-Nle-Asp-His-D-Phe-Arg-Trp-Lys-Gly-NH$_2$ ) induced an erection within 60 minutes following administration at a concentration of 2.5 mg. This erection lasted, intermittently, for up to six hours. A dose of 1.25 mg also induced an erection which took longer to initially occur, but which was also sustained intermittently for up to 6 hours. No stomach discomfort was experienced.

Still other of the listed peptides according to the present invention have also been shown to induce an erectile response at very low (1–3 mg) doses.

At the lower dose of the peptides that induce an erection, detumescence follows ejaculation which is another reason why the lower dosage is preferred. Following the initial detumescence, subsequent erections can follow (depending upon the dosage initially given) that are again relieved by detumescence. Thus, the peptides according to the present invention have not been found to cause a too prolonged rigidity (priapism) as is sometimes the problem with penile auto-injections of conventional therapies using drugs such as prostaglandins and papaverine.

In addition to providing a safe therapy for sexual dysfunction, the peptides of the present invention may also be administered subcutaneously or intramuscularly by the physician to provide a rapid and reliable estimation (diagnosis) of erectile potential. Use of the peptide will rapidly differentiate between the two major causes (psychogenic and vascular/organic) of dysfunction; it can be completed within 30 to 120 minutes; and can be self-evaluated in the home. Since the peptides according to the present invention have proven to be 100% effective in inducing an erection in normal volunteers, the present invention should become the new "gold standard" for the evaluation of erectile dysfunction. It should also be pointed out that the present methods of erectogenic evaluation are very time consuming and consequently very expensive to the patient.

It is interesting to note that a related peptide, i.e.

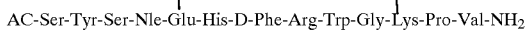

AC-Ser-Tyr-Ser-Nle-Glu-His-D-Phe-Arg-Trp-Gly-Lys-Pro-Val-NH$_2$ did not cause an erectile response at even the highest dose administered (about 20 mg). This suggests that the ability of the peptides according to the present invention relates to its structure.

In addition to bringing about an erectile response in human volunteers, it has also been determined that these peptides also bring about an erectile response when administered subcutaneously or intramuscularly into the rat or mouse. Furthermore, the peptide of Compound 11 when injected into the castrated dog caused no erectile response, but did so if the animal is first primed with testosterone. This suggests that the invention may prove effective in treating impotency in elderly men whose testosterone levels may be declining with age. These individuals, although classified as organically dysfunctional, should respond to the peptides of the present invention when it is administered separately or in conjunction with testosterone or other androgen.

An intriguing question relates to whether a peptide according to the present invention might have any effect on the female. Although no human trials have been conducted, peptides related to the present invention have been injected into the ventricles of the female rat brain resulting in the induction of lordosis (sexual posture), and following injection (subcutaneous) of the peptides according to the present invention into female rabbits has induced a tail-wagging response which is believed to be a behavioral response related to sexual excitement. It may be, therefore, that the peptides of the present invention may also be a means of stimulating the sexual response in females, including treatment (therapy) of the inhibited sexual desire syndrome.

The action seen in female rats and rabbits indicates an interesting potential for peptides according to the present invention in animal husbandry. The peptides according to the present invention may be administered, for example, to increase the libido of female animals belonging to rare species in captivity at the proper time in their oestrus cycle to make them more receptive to coitus, in addition to providing male animals with an increased libido resulting from an induced erectile response following administration of the peptide. Thus, the peptides according to the present invention may be used as an adjunct to present day breeding practices of both endangered and domesticated animals.

The peptides according to the present invention may also be used in artificial insemination programs. For example, the peptides may be administered to stallions which, for psychological and/or physical reasons will not mount a (mock) female phantom used in the collection of sperm. Also, the peptides according to the present invention may also be used as an alternative to the electro-ejaculator probe used in collecting semen from bulls in cattle breeding programs; rather than provide electric stimulation to bring about the erectile response in the bull needed to collect sperm, the peptides may be administered to the bull as a means of providing an erectile response, and the sperm may then be collected in an artificial vagina in the normal manner.

The present invention may also be used in clinics where the collection of sperm for artificial insemination is used, but in those instances wherein the individual has difficulties in achieving an erection.

In administering the erectogenic peptides of the present invention to an animal, including man, the peptides may be administered in a number of modalities including, for example, subcutaneous, intracorporeal or intramuscular injection; by topical solutions applied to the eye; by oral means such as pills, capsules and the like; and by topical salves, ointments and creams applied, for example, directly to the penis for transdermal administration. In each of these modalities, the peptides according to the present invention may be given alone or with other erectogenic peptides according to the present invention, or in combination with other erectogenic compounds such as papaverine. When administered, the peptides according to the present invention may also be in combination with, for example, appropriate fillers, buffers, solvents, carriers, extenders and other conventional materials known in the compounding arts for the formulations of appropriate injection solutions, topical solutions, pills, capsules, topical salves, ointments, creams and the like.

Thus, while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Such alterations and changes may include, for example, different pharmaceutical compositions for the administration of the peptides according to the present invention to a mammal; different amounts of peptide in the compositions to be administered; different times and means of administering the peptides according to the present invention; and different materials contained in the administration dose including, for example, combinations of different peptides, or combinations of erectogenic peptide with other biologically active (including but not limited to other erectogenic compounds) compounds. Such changes and alterations also are intended to include modifications in the amino acid sequence of the specific erectogenic peptides described herein in which such changes alter the sequence in a manner as not to change the erectogenic potential of the peptide, but as to change solubility of the peptide in the pharmaceutical composition to be administered or in the body, absorption of the peptide by the body, protection of the peptide for either shelf life or within the body until such time as the biological action of the peptide is able to bring about the desired effect, and such similar modifications. Accordingly, such changes and alterations are properly intended to be within the full range of equivalents, and therefore within the purview of the following claims.

Having thus described my invention and the manner and process of making and using it in such full, clear, concise and exact terms so as to enable any person skilled in the art to which it pertains, or with which it is most nearly connected, to make and use the same.

I claim:

1. A method for stimulating sexual response in females which comprises administering a peptide in an amount sufficient to bring about a sexual response in a female biologically and physically capable of achieving said response, said peptide being selected from the group consisting of:

Ac-Nle-Asp-His-D-Phe-Arg-Trp-Lys-NH$_2$;

Ac-Nle-Asp-His-D-Phe-Arg-Trp-Lys-NH$_2$ (cyclic);

Ac-Nle-Asp-His-D-Phe-Arg-Trp-Lys-Gly-NH$_2$ (cyclic);

Ac-Nle-Asp-His-D-Phe-Arg-Trp-Lys-Gly-Pro-NH$_2$ (cyclic);

Ac-Ser-Tyr-Ser-Nle-Asp-His-D-Phe-Arg-Trp-Lys-NH$_2$ (cyclic);

Ac-Tyr-Ser-Nle-Asp-His-D-Phe-Arg-Trp-Lys-NH$_2$ (cyclic); and

Ac-Ser-Nle-Asp-His-D-Phe-Arg-Trp-Lys-NH$_2$ (cyclic);

and a mixture of peptides taken from said group.

2. A method according to claim 1 in which the peptide is

Ac-Nle-Asp-His-D-Phe-Arg-Trp-Lys-NH$_2$.

3. A method according to claim 1 in which the peptide is

Ac-Nle-Asp-His-D-Phe-Arg-Trp-Lys-NH$_2$ (cyclic).

4. A method according to claim 1 in which the peptide is

Ac-Nle-Asp-His-D-Phe-Arg-Trp-Lys-Gly-NH$_2$ (cyclic).

5. A method according to claim 1 in which the peptide is

Ac-Nle-Asp-His-D-Phe-Arg-Trp-Lys-Gly-Pro-NH$_2$ (cyclic).

6. A method according to claim 1 in which the peptide is

Ac-Ser-Tyr-Ser-Nle-Asp-His-D-Phe-Arg-Trp-Lys-NH$_2$ (cyclic).

7. A method according to claim 1 in which the peptide is

Ac-Tyr-Ser-Nle-Asp-His-D-Phe-Arg-Trp-Lys-NH$_2$ (cyclic).

8. A method according to claim 1 in which the peptide is

Ac-Ser-Nle-Asp-His-D-Phe-Arg-Trp-Lys-NH$_2$ (cyclic).

* * * * *